United States Patent
Crossman

(10) Patent No.: US 6,719,771 B1
(45) Date of Patent: Apr. 13, 2004

(54) BLOOD SAMPLING DEVICE

(75) Inventor: David Danvers Crossman, Oxford (GB)

(73) Assignee: Owen Mumford Limited, Oxford (GB)

(*) Notice: Subject to any disclaimer, the term of this patent is extended or adjusted under 35 U.S.C. 154(b) by 40 days.

(21) Appl. No.: 10/018,370

(22) PCT Filed: Jun. 19, 2000

(86) PCT No.: PCT/GB00/02213

§ 371 (c)(1),
(2), (4) Date: Dec. 19, 2001

(87) PCT Pub. No.: WO00/78214

PCT Pub. Date: Dec. 28, 2000

(30) Foreign Application Priority Data

Jun. 19, 1999 (GB) .............................. 9914355

(51) Int. Cl.[7] .............................. A61B 17/14
(52) U.S. Cl. .................. 606/181; 606/182; 606/183; 606/184; 606/185
(58) Field of Search ................ 606/181–185; 600/136, 137; 604/192, 197, 198

(56) References Cited

U.S. PATENT DOCUMENTS

| | | | | |
|---|---|---|---|---|
| 3,358,689 A | * | 12/1967 | Higgins ........................ 606/181 |
| 3,760,809 A | * | 9/1973 | Campbell, Jr. ............... 606/182 |
| 5,147,375 A | * | 9/1992 | Sullivan et al. ............. 606/182 |
| D342,573 S | * | 12/1993 | Cerola ........................ D24/147 |
| 5,741,288 A | | 4/1998 | Rife |
| 5,797,940 A | * | 8/1998 | Mawhirt et al. ............ 606/167 |
| 5,908,434 A | * | 6/1999 | Schraga ...................... 606/181 |
| 5,951,493 A | * | 9/1999 | Douglas et al. ............. 600/583 |
| 6,197,040 B1 | * | 3/2001 | LeVaughn et al. .......... 606/182 |
| 6,514,270 B1 | * | 2/2003 | Schraga ...................... 606/182 |

FOREIGN PATENT DOCUMENTS

| | | |
|---|---|---|
| EP | 0 427 406 | 5/1991 |
| WO | WO 93/19671 | 10/1993 |
| WO | WO 98/58584 | 12/1998 |

* cited by examiner

Primary Examiner—Michael J. Milano
Assistant Examiner—D. Jacob Davis
(74) Attorney, Agent, or Firm—Young & Thompson

(57) ABSTRACT

A blood sampling device has a lancet (2) captive within a housing (1), to be released from a rearward primed position by pressing a trigger (18) on the side of the housing. A spring (3) shoots the lancet (2) forwards, momentarily to project its tip. The lancet (2) is initially held by a hooked tongue (25, 28) that latches behind a transverse web (10, 11) within the housing, the trigger action dislodging that engagement. The tongue (25) either springs back after release and so will abut the trigger (18) or the front of the web (10) if pushed back in an attempt to re-latch, or it will stay permanently deformed and thus be unable to re-engage the web (10). Alternatively, the trigger (18) may slice off the hook (28), making re-use impossible.

15 Claims, 3 Drawing Sheets

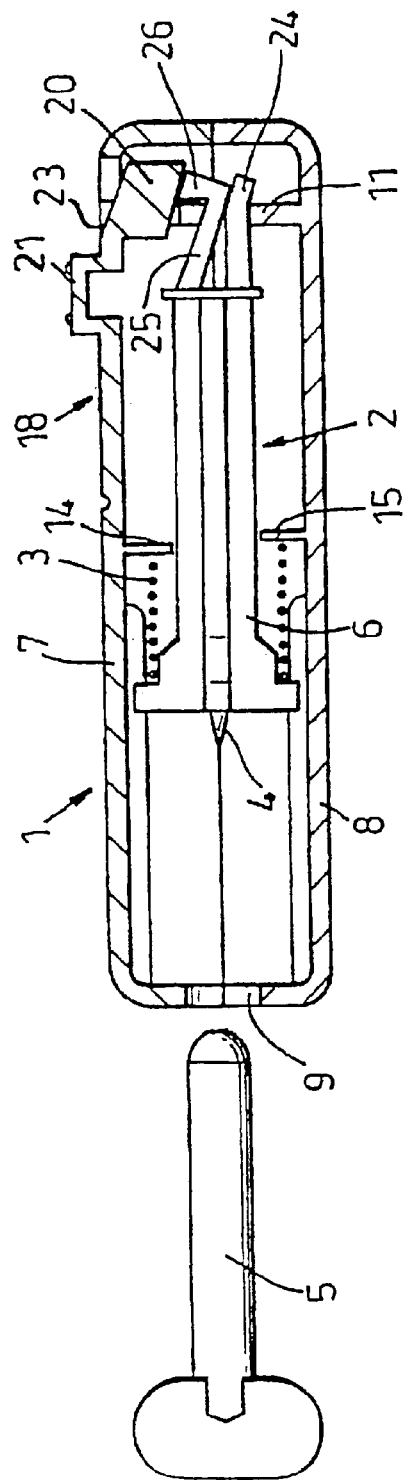
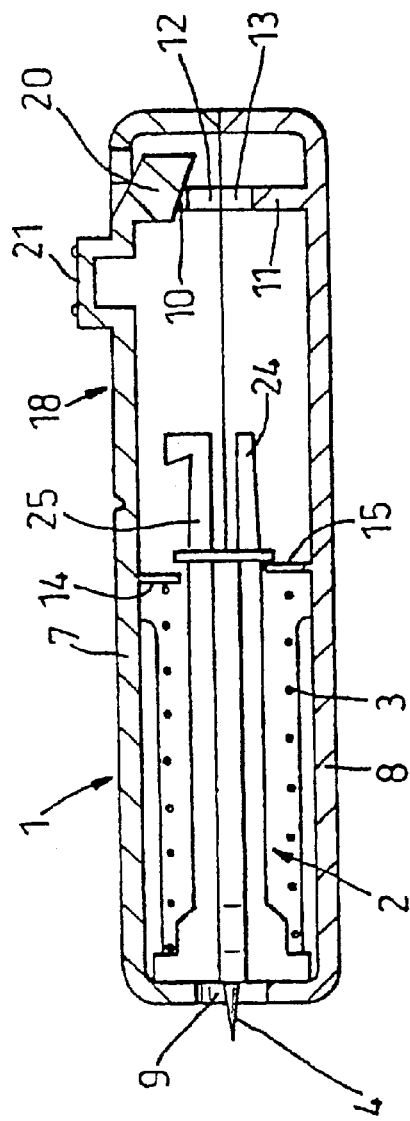

BLOOD SAMPLING DEVICE

BACKGROUND OF THE INVENTION

This invention relates to blood sampling devices.

DESCRIPTION OF THE RELATED ART

A common form of blood sampling device is a skin pricker comprising a spring loaded lancet in a small plastics housing with a trigger mechanism to release the lancet. Some require the lancet to be cocked or primed before being released, while others are assembled and sold in the cocked condition, ready to fire. But they are all quite simple and cheap, and can be thrown away after a single use.

A standard feature is that the lancet springs back a sufficient distance to retract the needle tip inside the housing after that tip has momentarily projected. Whilst that can give protection against subsequent injury, various measures have been devised to try to ensure that the user cannot reset the device and fire it again. This has certainly been made difficult, but the ideal is to make it impossible.

One solution to this has been proposed in EP-B-0 582 226, where the lancet has wings that initially rest against internal shoulders of the firing device, holding the lancet back against a drive spring. A push button at the rear end is pressed to force the wings to break off or fold back, allowing the drive spring to act and urge the lancet forwards. If the wings fold, as shown in FIG. 2 of the Patent, they will drag against the inside of the barrel of the firing device and impede retraction. In any event it is deemed necessary to provide a return spring. Also, the push button action and the radially projecting wings combine to require the rear end of the barrel to be rather bulky, first to provide the internal shoulders and secondly to provide external shoulders affording a grip for the user against the forward pressure of the push button. So it is not particularly compact and it requires a considerable number of components (barrel, two springs, push button and lancet) to be assembled.

SUMMARY OF THE INVENTION

It is the aim of this invention to provide a sleeker, non-reusable device with fewer components.

According to the present invention there is provided a blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, characterised in that the appendage extends rearwardly from the lancet and latches to a detent provided by the internal structure of the barrel, and in that the release of the lancet is by a trigger integral with the barrel being pressed in transversely to the barrel to unlatch the appendage.

Conveniently, the housing is an integral moulding with two halves hinged together to encase the lancet and a spring. Preferably, the trigger is an elongate element springing outwardly and rearwardly from one half of the barrel and with a rear end portion capable of projecting in through an aperture in the barrel to co-operate with the appendage. When actuated, the trigger may have a snap engagement with the barrel to retain it in its actuated position. This serves both as an indication that the device has been used and as a back-up for the non-recocking feature.

The appendage may have resilient flexure so that, after clearing the detent and trigger, it resumes its original position and will engage a portion of the retained trigger forward of the detent if the lancet is urged back towards its primed position. In the absence of any prior obstruction by the trigger, the latch can engage the forward side of the detent. Alternatively the appendage may have a weakness at its root causing it to stay bent after clearing the detent, so that if the lancet is urged back to its primed position, the appendage will not re-latch to the detent.

The detent is conveniently formed by two transverse webs which, when the halves are brought together, form an aperture through which the appendage extends. A finger may then project back parallel to the appendage from the rear end of the lancet and engage the edge of the aperture remote from the trigger, thereby ensuring that, when the trigger is pressed in, the lancet is maintained in its proper alignment.

In an alternative arrangement the rear end of the appendage has a narrow neck and a head which engages behind the detent over which the neck lies, and the trigger has a portion formed as a blade which initially registers with the neck and, when the trigger is pressed in, severs the neck to cause the head to fall free and the lancet to be sprung forwards.

The spring will generally be a helical spring that surrounds and is connected to the lancet, acts between the forward end thereof and an abutment forward of the detent, and extends beyond its relaxed state when driving the lancet forwards so that it withdraws the lancet tip into the barrel after the momentary projection. It is thus well clear of the part of the lancet that co-operates with the detent and does not will not interfere with the latching arrangement.

BRIEF DESCRIPTION OF THE DRAWINGS

For a better understanding of the invention, some embodiments will now be described, by way of example, with reference to the accompanying drawings, in which:

FIG. 4 is a longitudinal section of the pricker at the point of firing, FIG. 5 is a longitudinal section of the pricker at the moment of skin penetration.

DESCRIPTION OF THE PREFERRED EMBODIMENTS

Figure 1:
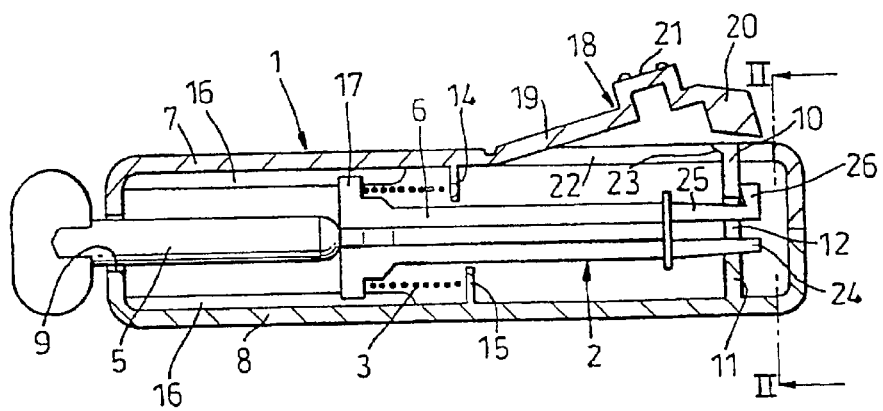
FIG. 1 is a longitudinal section of a finger pricker in its pre-use or "as sold" condition.
Figure 2:
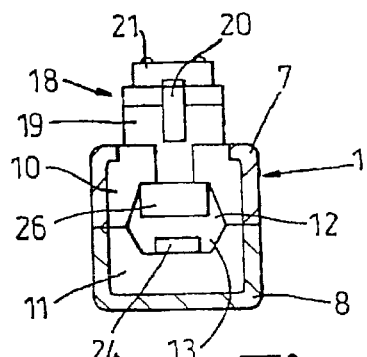
FIG. 2 is a cross-section on the line II—II of FIG. 1.
Figure 3:
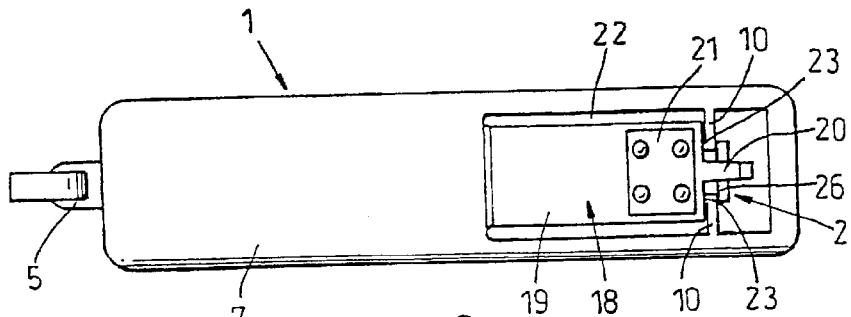
FIG. 3 is a plan view of the pricker.

The pricker comprises an elongate box-like housing 1 containing a lancet 2 and a spring 3, the tip 4 of the lancet needle initially being concealed within the rear end of an elongate cap 5 integrally moulded with the body 6 of the lancet. The housing 1 is also integrally moulded in two side-by-side channel-like upper and lower halves 7 and 8 with a thin web or a set of webs bridging adjacent sides and forming a hinge. These halves are subsequently folded together and adhered or welded to encase the lancet 2 and the spring 3. The rear end of the housing 1 is closed, but the forward ends of the halves 7 and 8 have semi-circular cut-outs which combine to form an aperture 9 through which the cap 5 extends.

A short distance forward from the rear end, the halves 7 and 8 have transverse webs 10 and 11 respectively. The web 10 is actually two separate portions, symmetrically opposed to form an inverted T-shaped gap 12, while the web 11 has a central cut-out 13 in its free edge. At about the mid-length of the housing 1 there are two further transverse webs 14 and 15 which are slightly staggered and stand marginally proud of their respective halves. When the halves 7 and 8 are closed together, the webs 14 and 15 overlap, but they have cut-outs at their free edges which combine to form a cruciform aperture, complementary to the cross-section of the lancet, which passes non-rotatably through that aperture. Opposed pairs of ribs 16 extend within each half from the leading end almost to the webs 14 and 15, providing grooves in which fingers of an enlarged head 17 of the lancet are guided. The spring 3 coils around the lancet and acts between this head 12, to which it is captive, and the webs 14 and 15.

A trigger 18 is formed as a tongue integral with the upper half 7. A wide portion 19 slopes outwardly and rearwardly from just behind webs 14 and at its end narrows immediately in front of the two-part web 10 into a central knife-like finger 20 angling back towards the housing. The upper side of the portion 19 has a finger pad 21. The formation of the trigger 18 leaves a generally rectangular aperture 22 spanned by the web 10 with the stem of whose T-shaped gap 12 the finger 20 registers. The plastics material of which the housing is moulded allows the trigger to be flexed in to project the finger 20 further into the gap 12 from the position shown in FIG. 1. On either side of the exposed mouth of the gap 12 the top edge of the web 10 has forward projecting lugs 23 which can snap over the free rear end of the portion 19 either side of the finger 20 when the trigger 18 is fully depressed, thereby retaining the trigger in that position after use. This is a further measure against re-use, beyond those described below, as well as a simple visual indication of the state of the device.

A finger 24 and a tongue 25 project rearwardly from the rear end of the lancet, the finger 24 being straight and the tongue 25 being L-shaped and thus having an outward undercut hook 26, forming a latch. This hook 26 is wider than the stem of the gap 12. Initially, the finger 24 extends through the cut-out 13 and the hook 26 is caught behind corners of the divided web 10 which are locally shaped to match the sloping undercut of the hook 26 and thus provide positive engagement which retains the lancet 2 in a rearward position with the spring 3 compressed.

Figure 6:
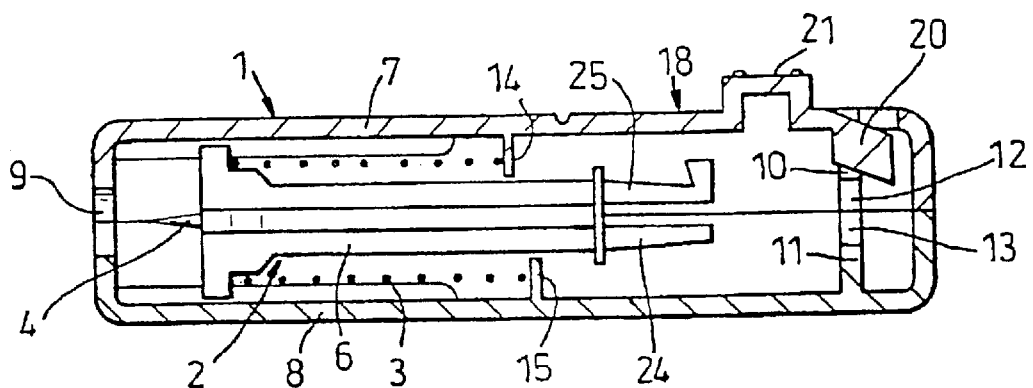
FIG. 6 is a longitudinal section of the pricker after use.

The finger pricker is assembled, packaged and sold in this condition. For use, the cap 5 is twisted and pulled, to remove it as shown in FIG. 4. The lancet is non-rotatable, as mentioned above, and is trapped in a rearward position by the hook 26. The forward end of the housing 1 is then applied to a finger and pressure is applied to the pad 21 of the trigger 18. The finger 20 meets the top of the hook 26 and bends the tongue 25 so that the hook 26 is disengaged with a snap (because of the undercut) from the web 10 and has a clear forward passage through the crossbar of the inverted T-shaped gap 12. The finger 24 may bend a bit as rather exaggeratedly shown in FIG. 4. However, the friction of the tip of the finger 20 on the hook 26 and that between the finger 24 and the web 11 is not sufficient to hold the lancet against the spring 3, and therefore the lancet is shot forwards, briefly to project the needle tip 4, as shown in FIG. 5. The lancet rebounds to the FIG. 6 position. Meanwhile, the trigger 18 is trapped in its depressed condition by the lugs 23.

Figure 7:
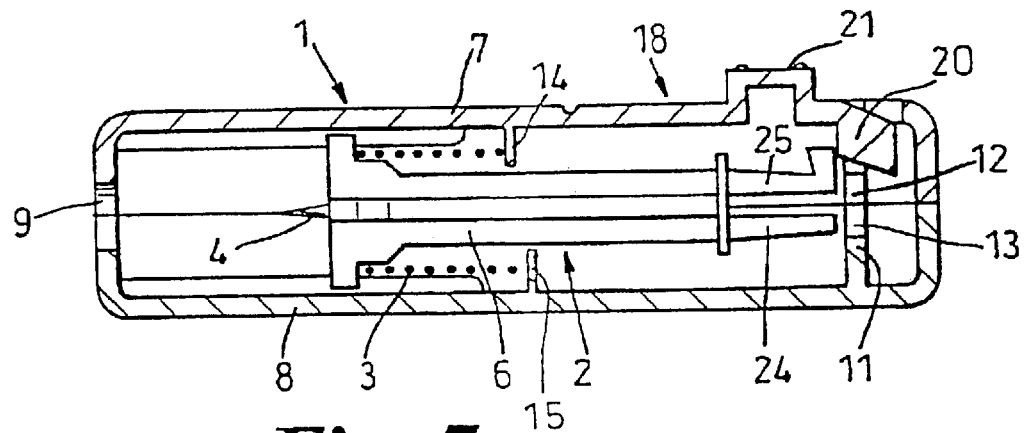
FIG. 7 is a longitudinal section of the pricker after use and with its lancet retracted in an attempt to re-set.

If someone tries to re-cock the device by pushing the lancet back by a poking implement through the aperture 9, the lancet will be arrested by the outside of the hook 26 coming up against the forward edge of the finger 20, as shown in FIG. 7. There is back-up to this, and even if the trigger was released the hook 26 would then meet the corners of the web 10 that previously retained it in the primed or cocked position. The hook 26 will still not be able to pass through the gap 12.

That assumes that the tongue 25 is resilient and resumes its original attitude as soon as it has cleared the gap 12 on being fired.

However it is possible to make the tongue 25 with a weakness and/or of a material such that, once bent to the position of FIG. 4 it remains there and does not recover. Then, although the lancet can be pressed further back after firing, with the trigger 18 sprung out to its initial position and the finger 24 and tongue 25 projecting through the cut-out 13 and gap 12, the hook 26 will not catch again, and as the poking implement is removed, the lancet will move forwards again to the position of FIG. 6.

Figure 8:
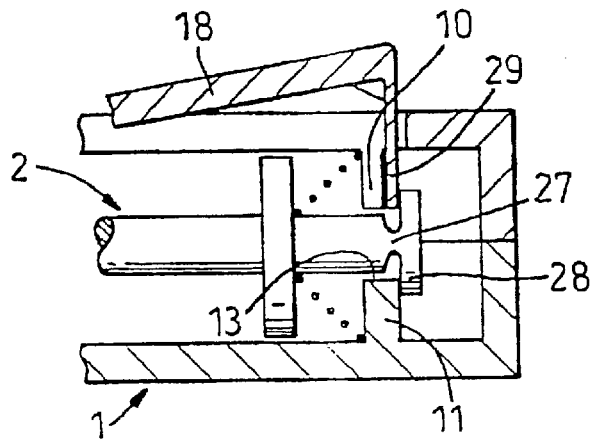
FIG. 8 is a detail, in longitudinal section, of another finger pricker in its primed condition.

Instead of bending or deforming the tongue 25, an alternative way of ensuring no re-use is shown in FIG. 8. At its rear end the lancet body narrows at a neck 27 and terminates in a head 28 that hooks behind the periphery of the cut-out 13 in the web 11. The web 11 is thicker than in the previous embodiment, its front face being level with that of the web 10 but with its rear face further back. The neck 27 is just to the rear of the web 10, and the trigger finger 18 terminates a transverse guillotine blade, also just to the rear of the web 10.

Pressing in the trigger slices off the head 27, the web 11 acting as an executioner's block. The head remains captive behind the webs 10 and 11 while the lancet projects forward and rebounds as described above. It will be appreciated that there is no way of re-capturing the lancet in its primed condition and re-firing it.

What is claimed is:

1. A blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, wherein, the appendage extends rearwardly from the lancet and latches to a detent provided by the internal structure of the barrel, the release of the lancet is by the trigger integral with the barrel being pressed in transversely to the barrel to unlatch the appendage, and the barrel is an integral molding with two halves hinged together to encase the lancet and the spring.

2. A blood sampling device as claimed in claim 1, wherein the trigger is an elongate element springing outwardly and rearwardly from one half of the barrel and with a rear end portion capable of projecting in through an aperture in the barrel to co-operate with the appendage.

3. A blood sampling device as claimed in claim 1, wherein the trigger, when actuated, has a snap engagement with the barrel to retain it in its actuated position.

4. A blood sampling device as claimed in claim 1, wherein the appendage has resilient flexure so that, after clearing the detent and trigger, it resumes its original position and will engage a portion of the trigger, in a retained position, forward of the detent if the lancet is urged back towards its primed position.

5. A blood sampling device as claimed in claim 1, wherein the appendage has resilient flexure so that, after clearing the detent, it resumes its original position and, in the absence of any prior obstruction by the trigger, will engage the forward side of the detent if the lancet is urged back towards its primed position.

6. A blood sampling device as claimed in claim 1, wherein the appendage has a weakness at its root causing it to stay bent after clearing the detent, so that if the lancet is urged back to its primed position, the appendage will not re-latch to the detent.

7. A blood sampling device as claimed in claim 1, wherein the detent is formed by two transverse webs in respective halves which, when the halves are brought together, form an aperture through which the appendage extends.

8. A blood sampling device as claimed in claim 7, wherein a finger projects back parallel to the appendage from the rear end of the lancet and engages the edge of the aperture remote from the trigger, thereby ensuring that, when the trigger is pressed in, the lancet is maintained in its proper alignment.

9. A blood sampling device as claimed in claim 1, wherein the appendage has a narrow neck and a head which engages behind the detent over which the neck lies, and wherein the trigger has a portion formed as a blade which initially registers with the neck and, when the trigger is pressed in, severs the neck to cause the head to fall free and the lancet to be sprung forwards.

10. A blood sampling device as claimed in claim 1, wherein the spring is a helical spring that surrounds and is connected to the lancet, acts between the forward end thereof and an abutment forward of the detent, and extends beyond its relaxed state when driving the lancet forwards so that it withdraws the lancet tip into the barrel after the momentary projection.

11. A blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, wherein, the appendage extends rearwardly from the lancet and latches to a detent provided by the internal structure of the barrel, the release of the lancet is by the trigger integral with the barrel being pressed in transversely to the barrel to unlatch the appendage, and the trigger, when actuated, has a snap engagement with the barrel to retain the trigger in its actuated position against subsequent reactivation.

12. A blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, wherein, the appendage extends rearwardly from the lancet and latches to a detent provided by the internal structure of the barrel, the release of the lancet is by the trigger integral with the barrel being pressed in transversely to the barrel to unlatch the appendage, and the appendage has resilient flexure so that, after clearing the detent and trigger, the appedage resumes its original position and will engage a portion of the trigger forward of the detent if the lancet is urged back towards its primed position.

13. A blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, wherein, the appendage extends rearwardly from the lancet and latches to a detent provided by the internal structure of the barrel, the release of the lancet is by the trigger integral with the barrel being pressed in transversely to the barrel to unlatch the appendage, and the appendage has resilient flexure so that, after clearing the detent, the appendages resumes its original position and, in the absence of any prior obstruction by the trigger, will engage the forward side of the detent if the lancet is urged back towards its primed position so that it cannot be reprimed.

14. A blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, wherein, the appendage extends rearwardly from the lancet and latches to a detent provided by the internal structure of the barrel, the release of the lancet is by the trigger integral with the barrel being pressed in transversely to the barrel to unlatch the appendage, and the appendage has a weakness at its root causing appendage to stay bent after clearing the detent, so that if the lancet is urged back to its primed position, the appendage will not re-latch to the detent.

15. A blood sampling device comprising a barrel containing a spring-loaded lancet releasable by a trigger from a primed rearward position, momentarily to project its tip from the forward end of the barrel, the lancet having a distortable or detachable appendage to engage the barrel and hold the lancet against a drive spring, wherein, the appendage extends rearwardly from the lancet and latches to a detent provided by the internal structure of the barrel, the release of the lancet is by the trigger integral with the barrel being pressed in transversely to the barrel to unlatch the appendage, the appendage has a narrow neck and a head which engages behind the detent over which the neck lies, and the trigger has a portion formed as a blade which initially registers with the neck and, when the trigger is pressed in, severs the neck to cause the head to fall free and the lancet to be sprung forwards.

* * * * *